(12) United States Patent
McAuley et al.

(10) Patent No.: US 10,124,138 B2
(45) Date of Patent: Nov. 13, 2018

(54) RESPIRATORY MASK SEALING INTERFACE

(71) Applicant: Fisher & Paykel Healthcare Limited, Auckland (NZ)

(72) Inventors: Alastair Edwin McAuley, Auckland (NZ); Mark McLaren, Auckland (NZ); Wen Dong Huang, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 845 days.

(21) Appl. No.: 14/603,153

(22) Filed: Jan. 22, 2015

(65) Prior Publication Data

US 2015/0128951 A1 May 14, 2015

Related U.S. Application Data

(63) Continuation of application No. 13/021,100, filed on Feb. 4, 2011, now Pat. No. 8,939,151, which is a
(Continued)

(51) Int. Cl.
*A61M 16/06* (2006.01)
*A61M 16/20* (2006.01)
(Continued)

(52) U.S. Cl.
CPC .... *A61M 16/0622* (2014.02); *A61M 16/0003* (2014.02); *A61M 16/0066* (2013.01);
(Continued)

(58) Field of Classification Search
CPC .............. A61M 16/06; A61M 16/0605; A61M 16/0616; A61M 16/0622;
(Continued)

(56) References Cited

U.S. PATENT DOCUMENTS 4,852,185 A 8/1989 Olson
4,907,584 A 3/1990 McGinnis
(Continued)

FOREIGN PATENT DOCUMENTS

WO WO 2005/053781 A1 6/2005
WO WO 2005/118040 A1 12/2005
(Continued)

OTHER PUBLICATIONS

International Search Report; PCT/NZ2009/000157; dated Nov. 17, 2009; 4 pages.

*Primary Examiner* — Michael Tsai

(74) *Attorney, Agent, or Firm* — Knobbe, Martens, Olson & Bear, LLP

(57) ABSTRACT

A sealing interface forms part of an apparatus for supplying a flow of respiratory gases to a user. The sealing interface comprises a foam or gel inner cushion and a thin resilient rubber outer sheath. A face side of the inner cushion resiliently supports the outer sheath. The inner cushion has a toothed profile formed on the face side of the inner cushion. The toothed profile consists of at least one tooth having an apex on the perimeter of the inner cushion. The apex is positioned between two valleys in the perimeter of the inner cushion. In use the apex of each tooth of the toothed profile is in supporting contact with the outer sheath.

12 Claims, 21 Drawing Sheets

Related U.S. Application Data continuation of application No. PCT/NZ2009/000157, filed on Aug. 4, 2009.

(60) Provisional application No. 61/086,051, filed on Aug. 4, 2008.

(51) Int. Cl.
*A61M 16/16* (2006.01)
*A61M 16/00* (2006.01)
*A61M 16/10* (2006.01)

(52) U.S. Cl.
CPC ............ *A61M 16/06* (2013.01); *A61M 16/20* (2013.01); *A61M 16/0069* (2014.02); *A61M 16/0633* (2014.02); *A61M 16/0683* (2013.01); *A61M 16/109* (2014.02); *A61M 16/1095* (2014.02); *A61M 16/16* (2013.01); *A61M 2016/003* (2013.01); *A61M 2016/0027* (2013.01); *A61M 2205/3334* (2013.01); *A61M 2205/3368* (2013.01); *A61M 2205/3653* (2013.01); *A61M 2205/52* (2013.01)

(58) Field of Classification Search
CPC ........ A61M 2016/661; A61M 16/0627; A62B 18/00; A62B 18/02; A62B 18/025; A62B 18/04; A62B 18/08; A62B 18/082; A41D 13/11; A41D 13/1107; A41D 13/1176
See application file for complete search history.

(56) References Cited

U.S. PATENT DOCUMENTS

| | | |
|---|---|---|
| 4,910,804 A | 3/1990 | Lidgren |
| 5,303,423 A | 4/1994 | Gazzra et al. |
| 6,427,254 B1 | 8/2002 | Gardner |
| 6,505,353 B2 | 1/2003 | Sung |
| 7,308,895 B2 | 12/2007 | Wixey et al. |
| 8,939,151 B2 | 1/2015 | McAuley et al. |
| 2003/0229935 A1* | 12/2003 | Chou ............... A61F 9/026 2/440 |
| 2008/0257354 A1* | 10/2008 | Davidson ........... A61M 16/06 128/206.24 |
| 2009/0014007 A1* | 1/2009 | Brambilla ........... A61M 16/06 128/206.24 |

FOREIGN PATENT DOCUMENTS

WO WO 2005/123166 A1 12/2005
WO WO 2006/074513 A1 7/2006

\* cited by examiner

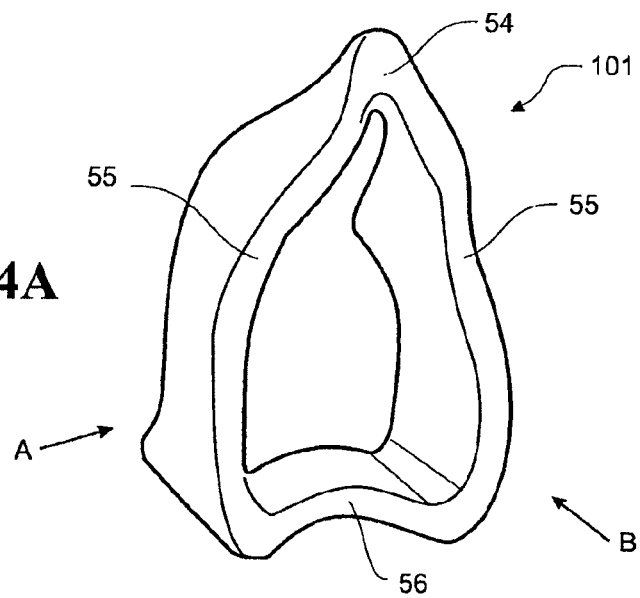
FIGURE 4A
(prior art)
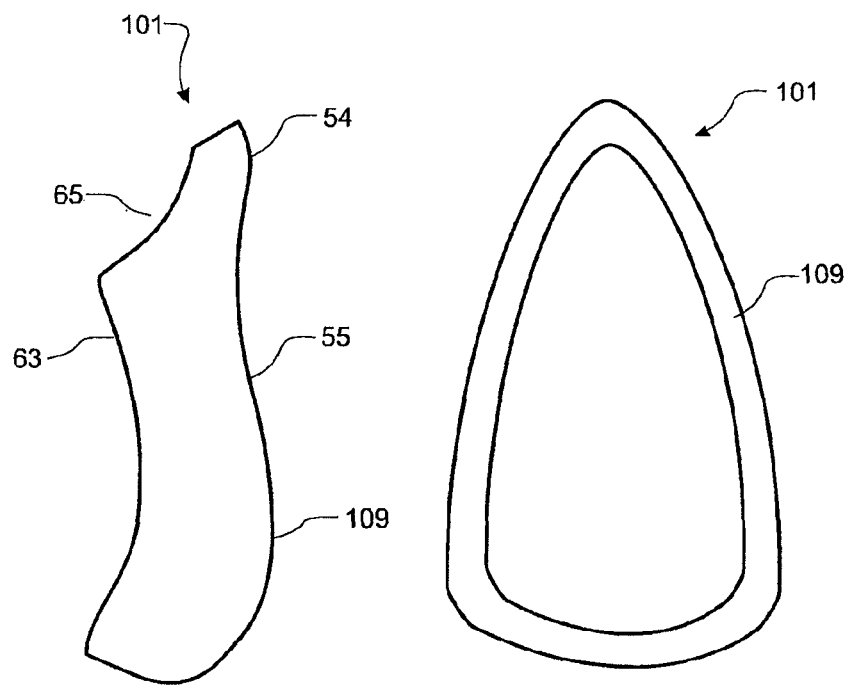
FIGURE 4B
(prior art)
FIGURE 4C
(prior art)

RESPIRATORY MASK SEALING INTERFACE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present invention generally relates to a sealing interface for use as part of an apparatus for supplying a flow of respiratory gases to a user.

Description of the Related Art

It is known to provide a flow of respiratory gases to a user via an interface, such as a face mask, to relieve a number of ailments, such as, for example, sleep apnea or snoring. One problem with supplying a flow of gases to a user via an interface, such as a face mask, is that it can be difficult to form a good seal between the mask and the face. The mask often is held in place against the user's face by headgear worn on the user's head. In use, the head gear may be over tightened and the mask is pressed uncomfortably onto the user's face. Alternatively, the headgear may be under tightened, or applied to the user's head too loosely, preventing the formation of an effective seal between the mask and user's face.

Prior face masks have attempted to improve the seal between the user's face and the mask and to make the sealing interface with the user more comfortable. U.S. Pat. No. 7,308,895 describes a mask assembly having a seal outer sheath and an inner cushion. The inner cushion has a raised nasal bridge portion that results in a more flexible seal contact on the bridge of the user's nose. The raised nasal bridge portion is formed by a cut out portion of the inner cushion with the cut-out being on a mask body side of the cushion.

U.S. Pat. No. 6,112,746 describes a nasal mask cushion for sealing a nasal mask to a user's face. The cushion has a first membrane and a second membrane. The second membrane contacts a user's face when in use. The second membrane is thinner than the first membrane and is spaced apart from the first membrane when the mask is not in use. The second membrane also is spaced from the first membrane by a greater distance in the nasal bridge region than in the cheek region.

In this specification, where reference has been made to patent specifications, other external documents, or other sources of information, this is generally for the purpose of providing a context for discussing certain features, aspects or advantages of the invention. Unless specifically stated otherwise, reference to such documents and information is not to be construed as an admission that such documents, or such sources of information, in any jurisdiction, are prior art, or form part of the common general knowledge in the art.

SUMMARY OF THE INVENTION

It is an object of the present invention to provide an improved sealing interface, or to at least provide the industry or the public with a useful choice.

In one aspect, the present invention consists in a sealing interface for use as part of an apparatus for supplying a flow of respiratory gases to a user comprising:

a resilient rubber outer sheath and a foam or gel inner cushion, in use the outer sheath covering the inner cushion, the outer sheath having a sheath first side, the sheath first side substantially sealing against a user's face, a face side of the inner cushion resiliently supporting at least a portion of the sheath first side, the inner cushion having a toothed profile in the face side of the inner cushion, the toothed profile comprising at least one tooth having an apex between two valley portions in the perimeter of the face side of the inner cushion, in use the apex being in supporting contact with the outer sheath first side.

Preferably the toothed profile extends substantially around the full perimeter of the inner cushion first side.

Preferably the sheath first side and the cushion first side have a nasal bridge region, either one of an upper lip region or a chin region and a left cheek region and a right cheek region extending between the nasal bridge region and the upper lip or chin region, and a said toothed profile is in the upper lip region or chin region.

Preferably a said toothed profile is in a lower portion of each of the left and right cheek regions.

Preferably a said toothed profile is in nasal bridge region.

Preferably the at least one tooth has at least two converging sides, each said converging side having an angle of convergence, the angle of convergence being at least 30 degrees.

Preferably the tooth has a depth, the depth being approximately 3 mm to 10 mm.

Preferably the tooth has a base, the base being approximately 2 mm to 20 mm wide.

Preferably the at least one tooth is aligned inwards towards a centre of the inner cushion, a side of the at least one tooth being coterminous with the face side of the inner cushion and an opposite side of the at least one tooth being conterminous with an inside surface of a perimeter wall of the inner cushion, an apex of said at least one tooth being formed where the inside surface of the perimeter wall meets the face side of the inner cushion.

Preferably the toothed profile comprises a plurality of teeth, in use each said tooth having an apex in supporting contact with the sheath first side.

Preferably each said tooth has an apex, a distance between the apex of adjacent teeth being less than approximately 20 mm.

Preferably each said tooth has a depth, and a ratio of the tooth depth over the tooth pitch is at least approximately 0.3, wherein the pitch is the distance between the apexes of adjacent teeth.

Preferably the tooth depth decreases as the toothed profile extends from a central position of the toothed profile to a side of the toothed profile extending along the perimeter of the sealing interface.

Preferably the inner cushion comprises a plurality of spaced apart cushions, as said cushion being a tooth of the toothed profile.

Preferably the spaced apart cushions are joined by joining elements.

Preferably the inner cushion has at least two holes through a perimeter wall of the inner cushion, the at least two holes breaking the face side of the inner cushion to create the at least one tooth between said holes.

A second aspect consists in a sealing interface for use as part of an apparatus for supplying a flow of respiratory gases to a user comprising:

a thin resilient rubber outer sheath and a foam or gel inner cushion, in use the outer sheath covering the inner cushion, the outer sheath having a sheath first side, the sheath first side substantially sealing against a user's face, a face side of the inner cushion resiliently supporting at least a portion of the sheath first side, the inner cushion having a perimeter wall, and at least two holes through the perimeter wall adjacent the face side of the inner cushion.

A third aspect consists in a sealing interface for use as part of an apparatus for supplying a flow of respiratory gases to a user comprising:

a thin resilient rubber outer sheath and a foam or gel inner cushion, in use the outer sheath covering the inner cushion, the outer sheath having a sheath first side, the sheath first side substantially sealing against a user's face, a face side of the inner cushion resiliency supporting at least a portion of the sheath first side, and at least two cavities in the face side of the inner cushion.

A fourth aspect consists in a mask assembly for use as part of an apparatus for supplying a flow of respiratory gases to a user comprising:

a mask body having an inlet through which said flow of respiratory gases are provided to the interior of said mask body, the inlet adapted to in use be connected to a gases conduit, and a sealing interface coupled to the mask body, the sealing interface comprising:

a thin resilient rubber outer sheath and a foam or gel inner cushion, in use the outer sheath covering the inner cushion, the outer sheath having a sheath first side, the sheath first side substantially sealing against a user's face, a face side of the inner cushion resiliency supporting at least a portion of the sheath first side, the inner cushion having a toothed profile in the face side of the inner cushion, the toothed profile comprising at least one tooth having an apex between two valley portions in the perimeter of the face side of the inner cushion, in use the apex being in supporting contact with the outer sheath first side.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth

BRIEF DESCRIPTION OF THE DRAWINGS

Preferred embodiments of the invention will be described by way of example only and with reference to the drawings, in which:

FIG. 4a is a perspective view of a prior sealing interface inner cushion.

FIG. 4b is a side view of the prior sealing interface inner cushion of FIG. 4a, when viewed in the direction of arrow A.

FIG. 4c is an end view of the prior sealing interface inner cushion of FIG. 4a, when viewed in the direction of arrow B.

DETAILED DESCRIPTION OF THE PREFERRED EMBODIMENT

A sealing interface that is arranged and configured in accordance with certain features, aspects and advantages of the present invention provides improvements in the delivery of CPAP therapy. In particular a sealing interface is described that reduces a pressure of a mask on a face of a user and that reduces leakage when compared with the prior art. The sealing interface as described herein can be used in respiratory care generally or with a ventilator but will be described below with reference to use in a humidified CPAP system. Certain features, aspects and advantages of the present invention can be applied to any form of interface including, but not limited to, full face masks that seal around a nose and a mouth of a user, nasal masks that seal around a nose of a user, and oral masks and mouthpieces that are in sealing engagement with a mouth of the user.

Figure 1:
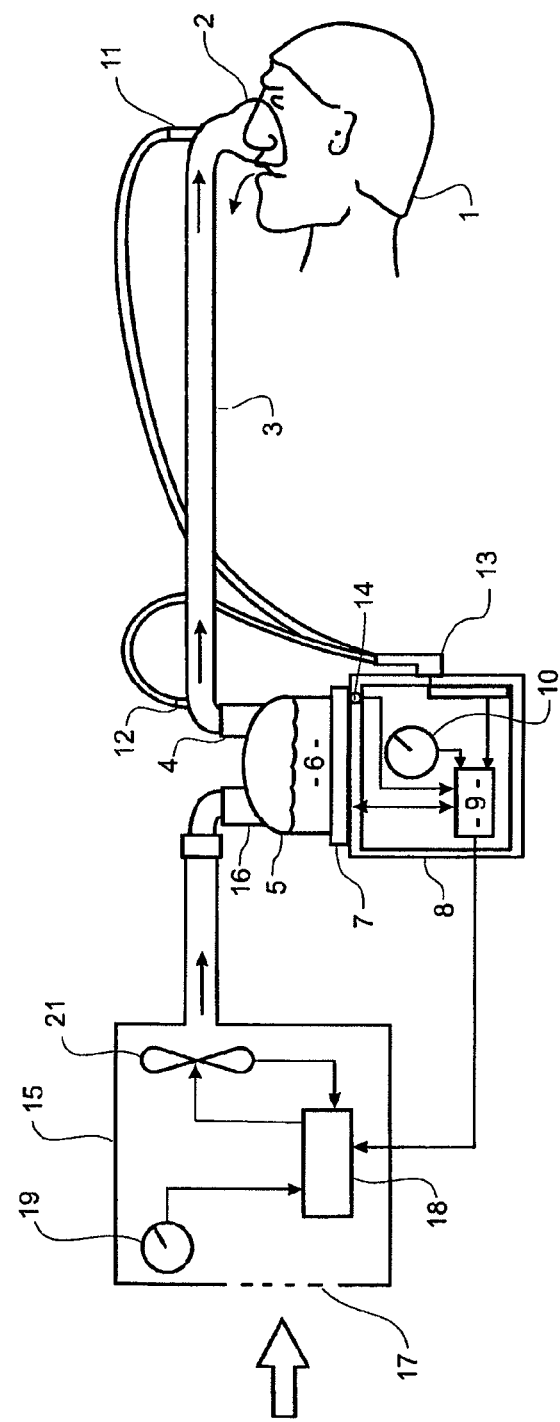
FIG. 1 is a block diagram of a system, such as a continuous positive airway pressure system, for providing a heated humidified gases stream to a user as might be used in conjunction with a sealing interface that is arranged and configured in accordance with certain features, aspects and advantages of the present invention.

With reference to FIG. 1 a humidified Continuous Positive Airway Pressure (CPAP) system is shown in which a user 1 is receiving humidified and pressurized gases through an interface 2 that is connected to a humidified gases transportation pathway or inspiratory conduit 3. Delivery systems could also be VPAP (Variable Positive Airway Pressure), BiPAP (Bi-level Positive Airway Pressure) or any of numerous other forms of respiratory therapy. An inspiratory conduit 3 is connected to the outlet 4 of a humidification chamber 5, which contains a volume of water 6. The inspiratory conduit 3 may contain heating means or heater wires (not shown) that heat the walls of the conduit to reduce condensation of humidified gases within the conduit 3. The humidification chamber 5 preferably is formed from a plastics material and may have a highly heat conductive base (for example, an aluminum base) that is in direct contact with a heater plate 7 of a humidifier 8. The humidifier 8 is provided with control means or an electronic controller 9 that may comprise a microprocessor-based controller that executes computer software commands stored in an associated memory.

The controller 9 receives input from sources, such as user input means or a dial 10 through which a user of the device may, for example, set a predetermined required value (e.g., preset value) of humidity or temperature of the gases supplied to user 1. The controller 9 also may receive input from other sources, such as, for example, temperature and/or flow velocity sensors 11, 12 through a connector 13 and a heater plate temperature sensor 14. In response to the user set humidity or temperature value, which is input via the dial 10, and the other inputs, the controller 9 determines when, or to what level, to energise the heater plate 7 to heat the water 6 within the humidification chamber 5. As the volume of water 6 within the humidification chamber 5 is heated, water vapor begins to fill the volume of the chamber 5 above the water's surface and the water vapor is passed out of the outlet 4 of the humidification chamber 5 with the flow of gases (for example, air) that is provided from a gases supply means or a blower 15, which flow enters the chamber through an inlet 16. Exhaled gases from the mouth of the user can be passed directly to ambient surroundings in FIG. 1.

The blower 15 can be provided with variable pressure regulating means or a variable speed fan 21 that draws air or other gases through a blower inlet 17. The speed of the variable speed fan 21 is controlled by an electronic controller 18 (or alternatively the function of the controller 18 could carried out by the controller 9) in response to inputs from the controller 9 and a user-set predetermined required value (e.g., preset value) of pressure or fan speed, which is set via a dial 19, for example.

Interface

Figure 2:
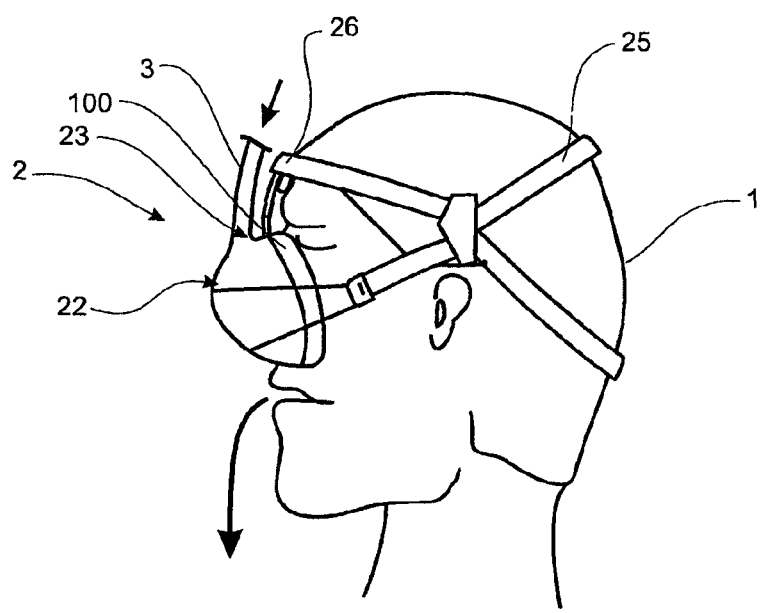
FIG. 2 is a diagram of a nasal mask that may incorporate a sealing interface that is arranged and configured in accordance with certain features, aspects and advantages of the present invention.

An interface in the form of a nasal mask 2 is shown in FIG. 2. The mask 2 comprises a hollow body 22 with an inlet 23 that is connected to the inspiratory conduit 3. The mask 2 is positioned around the nose of the user 1 with headgear 25 secured around a back of a head of the user 1. A restraining force from the headgear 25 on the hollow body 22 and a forehead rest 26 provides sufficient compressive force on a mask seal 100 to provide an effective seal against the face.

The hollow body 22 is constructed of a relatively inflexible material, such as, for example, polycarbonate plastic. Such a material would provide a desired rigidity, would be transparent and would be a relatively good insulator. The expiratory gases can be expelled through a valve (not shown) in the mask 2, a further expiratory conduit (not shown), vent paths through the mask 2 (not shown), or any other suitable method.

Mask Seal

The mask seal 100 is provided around a periphery of the mask body 22. The mask seal 100 provides an effective seal onto the face of the user to reduce the likelihood of leakage. The mask seal 100 is shaped to approximately follow the contours of the face of the user. The seal is contoured to approximately match the facial contours of the user around the nose, from a bridge of the nose, continuing down the cheek regions adjacent each side of the nose and across a philtrum area of the user (i.e., where a nasomedial and maxillary processes meet). Similarly, if the seal 100 was applied to a full face mask covering a user's nose and mouth, the seal would be shaped to approximate the facial contours of the chin and wider cheek regions. The seal 100 will deform when pressure is applied by the headgear 25 to adapt to individual contours of most users.

Figure 3:
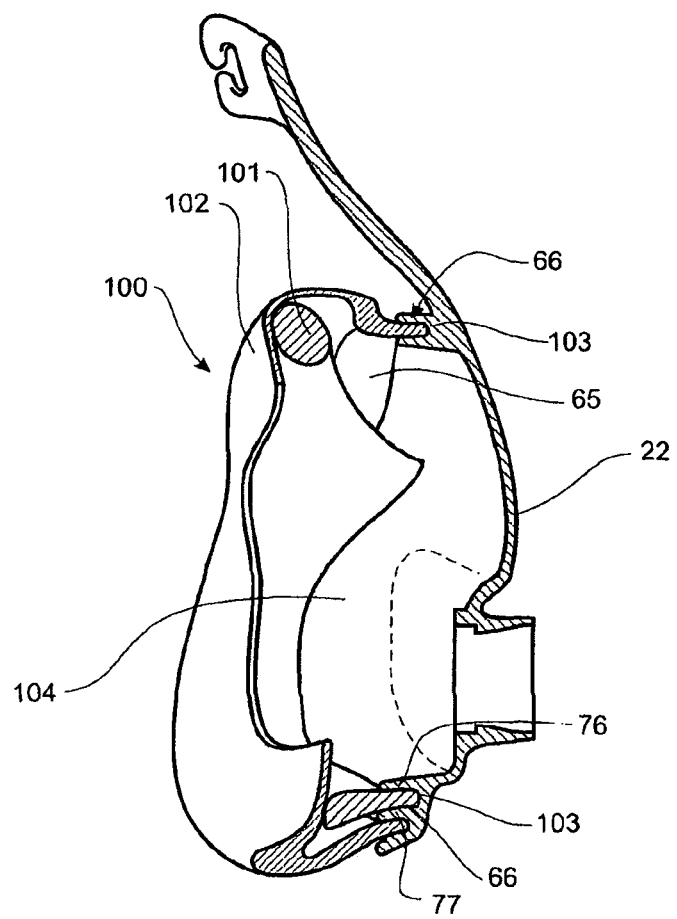
FIG. 3 is a cross sectional view of a face mask that may incorporate a sealing interface that is arranged and configured in accordance with certain features, aspects and advantages of the present invention.

A prior full face mask assembly and mask seal arrangement for sealing around the nose and the mouth of the user is shown in FIG. 3. The illustrated mask seal 100 comprises an inner foam cushion 101 covered by an outer sealing sheath 102. The inner cushion 101 is constructed of a resilient material, such as, for example, polyurethane foam, to distribute pressure along the seal 100 around the face. In other forms, the cushion 101 may be formed of other appropriate materials, such as a gel material, for example.

One side of the illustrated inner cushion 101 is shaped to approximately match the shape of the face of the user. As shown in FIG. 4, the inner cushion 101 can comprise an indented section 54 that is intended to fit over the bridge of the nose of the user, a cheek contour 55 on each side to follow the cartilage extending from the middle of the nose of the user, and an indented section 56 to seal around the chin area of the user. An opposite side of the cushion 63 is shaped to match and interface with the mask body 22.

The inner cushion 101 may include a raised bridge 65 in the nasal bridge region. The raised bridge 65 can also be described as a valley formed in the cushion 101 on a mask body side 63 of the cushion. Because the raised bridge 65 is unsupported by the mask body 22, it is much more flexible and results in less pressure on the nasal bridge of the user. In other forms, the cushion may have other bridge portions, so that in these bridging areas the cushion 101 is more flexible.

The inner cushion 101 is located around an inner periphery 103 of an open face 104 of the hollow body 22. The inner cushion 101 contacts the mask body, except for in the raised bridge portion 65. As best shown in FIG. 3, the cushion is located in a cavity 66 that extends around the inner periphery 103 of the body 22. The cavity 66 terminates at each side of the nose bridge region 67 of the mask, where the raised bridge portion 65 of the cushion generally does not contact the mask body 22. The cavity 66 generally is formed by two spaced apart walls 76, 77 that extend around the inner periphery of the mask.

Similarly, the outer sheath 102 is attached to an outer periphery of the mask body 22, either directly to the body 22 in a push fit arrangement as shown in FIG. 3 or indirectly via a mask seal clip (not shown), for example. Preferably, a side of the outer sheath 102 is attached to a seal clip (not shown). The seal clip interfaces with the mask body 22. The clip provides a releasable rigid or semi rigid interface, which allows the seal to be easily attached and detached from the mask body many times. The outer sheath 102 surrounds and loosely covers over the top of the inner cushion 101.

One side of the outer sheath 102 also is shaped to match the facial contours of the face of the user. The outer sheath preferably closely matches the shape of the side of the inner cushion 101 adjacent the face of the user in use.

Preferably, the inner cushion 101 is a separate item with the outer sheath 102 fitting in place over the inner cushion 101. In the preferred embodiment, the outer sheath 102 holds the inner cushion 101 in place within the mask assembly 2. Alternatively, the inner cushion 101 may be permanently or releasably attached to the outer sheath 102 so that the outer sheath 102 and the inner cushion 101 may be provided as a single assembly. Alternatively, the inner 101 cushion may be permanently or releasably attached to the mask body 22. In a further alternative, the outer sheath 102 and the inner cushion 101 may be integrally formed.

Toothed Profile

Figure 5A:
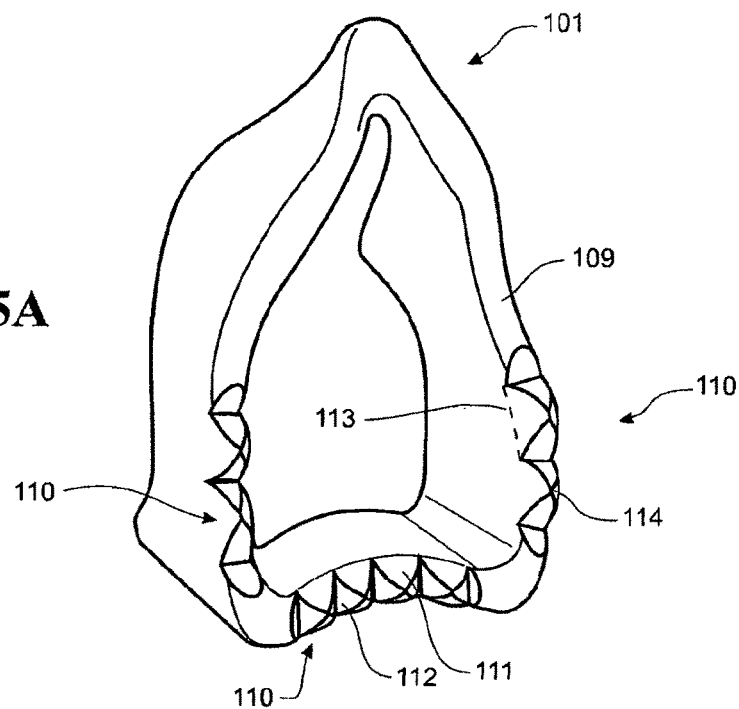
FIG. 5a is a sealing interface inner cushion that is arranged and configured in accordance with certain features, aspects and advantages of a first embodiment of the present invention.
Figure 5B:
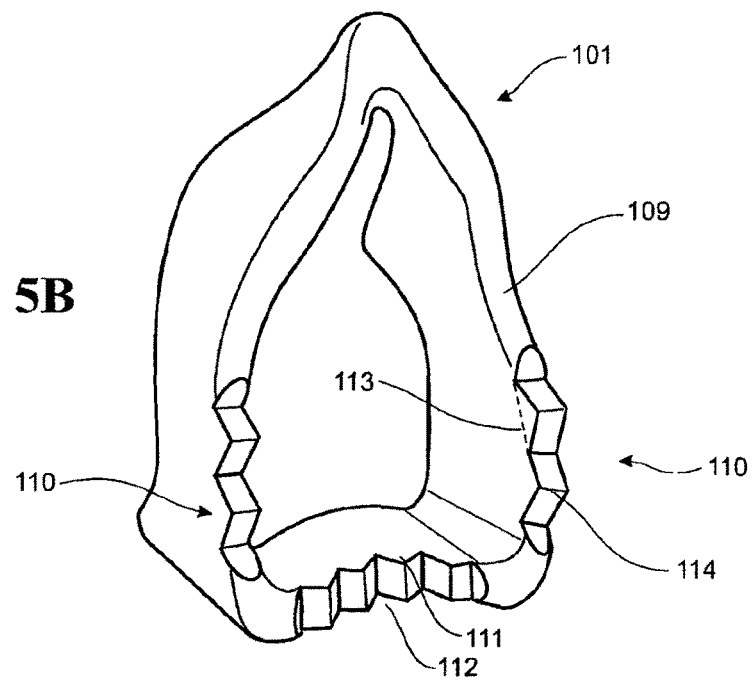
FIG. 5b is a sealing interface inner cushion that is arranged and configured in accordance with certain features, aspects and advantages of a second embodiment of the present invention.

As shown in FIGS. 5 to 7, certain features, aspects and advantages of the present invention can be exemplified in a mask cushion designed for use in a mask assembly, such as the mask assembly described above. Like the inner cushion of the prior sealing interface, the inner cushion 101 that is arranged and configured according to certain embodiments of the present invention is constructed of a resilient material, preferably polyurethane foam, to distribute pressure along the seal around the face of the user. In other forms, the present cushion 101 may be formed of other appropriate materials, such as a gel material, for example. The inner cushion 101 may be formed from any suitable resilient material having similar stiffness to a two part polyurethane foam with a density of approximately 0.20-0.25 g/cm3.

The outer sheath 102 is a thin resilient rubber material that is used to form a seal against the face of the user in use. Preferably, the outer sheath 102 is formed from silicone.

The mask cushion 101, when arranged and configured in accordance with certain features, aspects and advantages of one embodiment of the present invention, has a toothed profile 110 on the side of the cushion 101 that bears against face of the user when in use. The outer sheath 102 would be located between the face of the user and the toothed profile during in use. One significant advantage of such a construction is that the valleys 112 of the toothed profile 110 are on the user face side 109 of the cushion.

Having the toothed profile 110 on the face side of the cushion 101 is believed to result in an improved seal for a given sealing force. To create an effective seal on the face, the head gear 25 is tightened sufficiently to compress the cushion 101 against the face. The toothed profile 110 helps achieve an effective seal using a lower sealing force than a similar inner cushion without the toothed profile 110. This results in a more comfortable interface. A user can use the mask 2 with a lower sealing force, such that the headgear and the mask assembly can be applied to the head and face with less tension in the head gear straps, which results in a lower compressive force of the seal 100 on the face. The lower compressive force results in less irritation over an extended use period. With less irritation, users are more likely to use the mask and to adhere to treatment requirements. Thus, increased compliance results from the improved cushion structure.

Figure 6A:
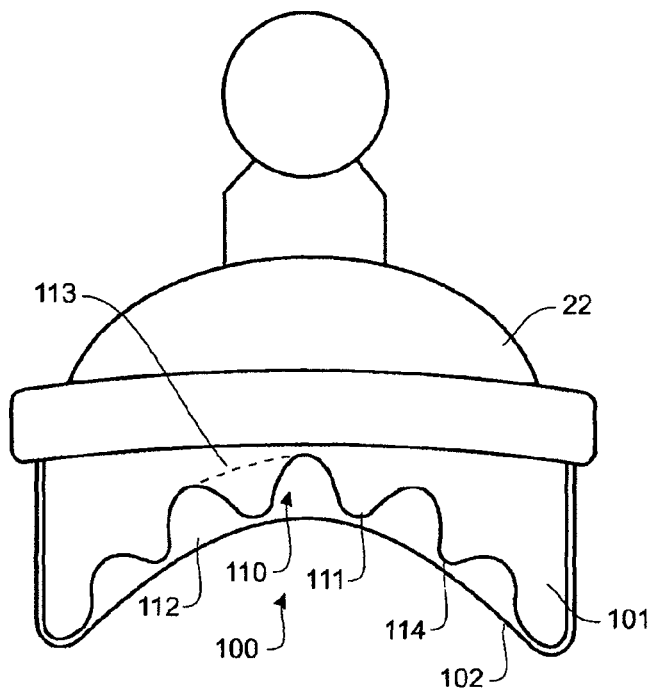
FIGS. 6a-6e are bottom views of a face mask that show face masks that are arranged and configured in accordance with certain features, aspects and advantages of various embodiments of the sealing interface of the present invention.
Figure 6B:
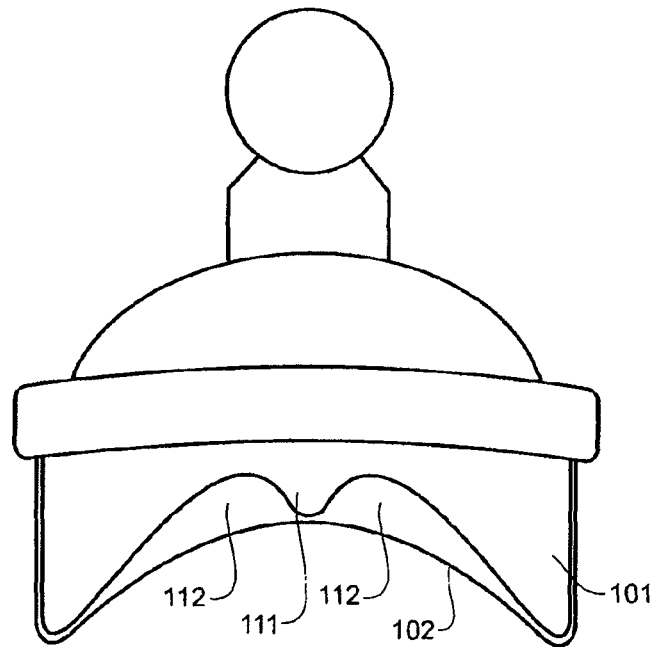
Figure 6C:
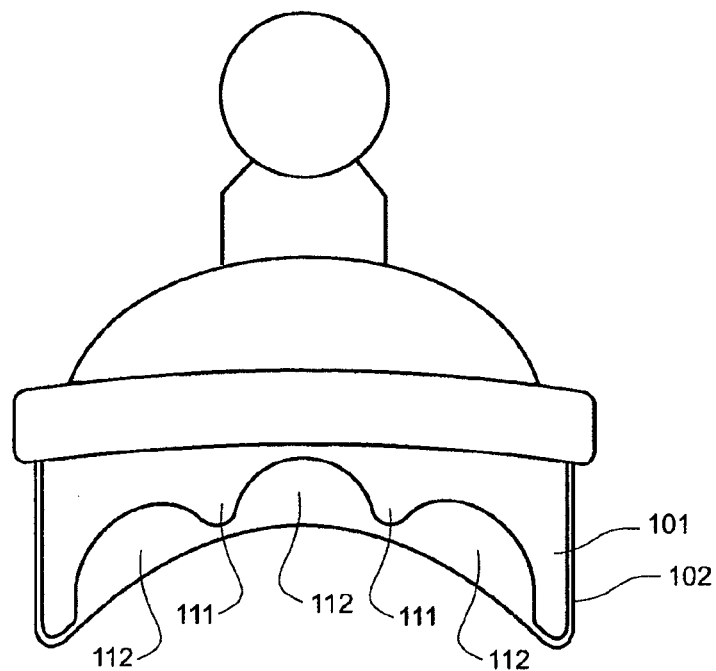
Figure 6D:
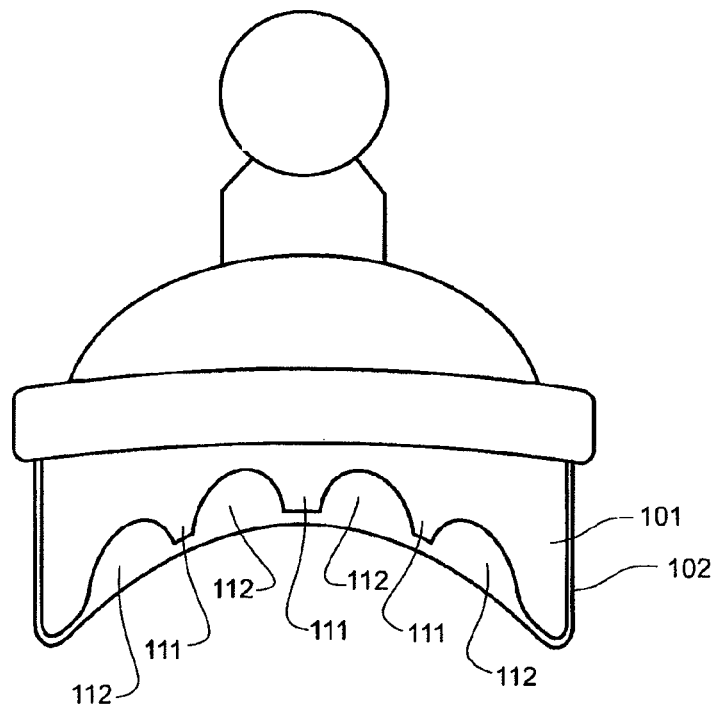
Figure 6E:
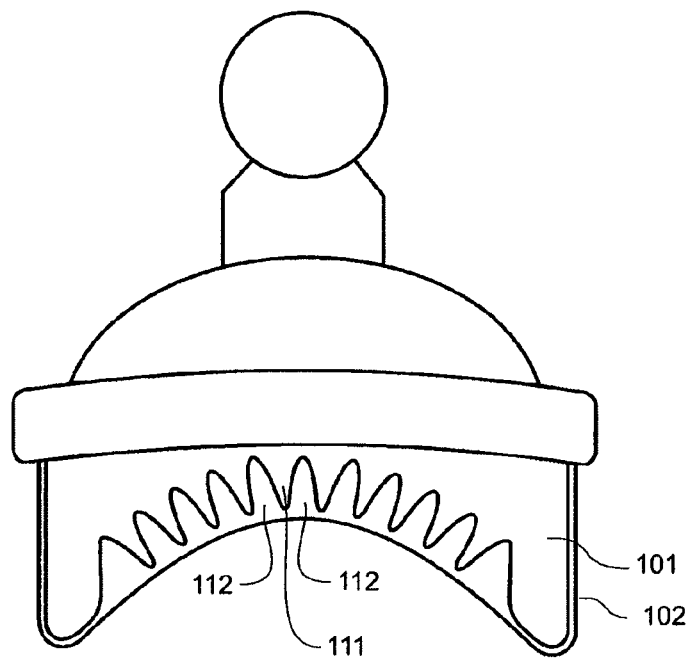
Figure 6F:
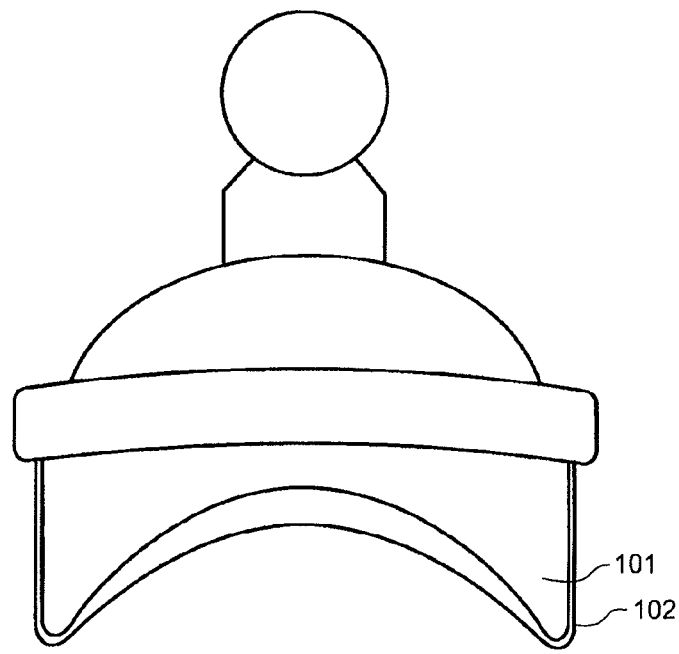
FIG. 6f is a bottom view of a face mask with a prior sealing interface arrangement having a gap between an inner cushion and an outer sheath.

Some prior masks comprise a gap between the outer sheath 102 and the inner cushion 101 as shown in FIG. 6f. The mask of FIG. 6f is shown when not in use. In use, the gap between the outer sheath 102 and the inner cushion 101 may or may not close, depending on the sealing force applied to the sealing interface. However, an improvement has been discovered. Providing discrete points or areas 114 of support for the outer sheath when in use is believed to improve the performance of the mask. The contact support points or areas are spaced apart along the perimeter of the mask sealing interface.

The illustrated toothed profile consists of at least one tooth 111 having an apex 114 on the perimeter of the cushion. The apex 114 is positioned between two valleys 112 in the perimeter of the cushion 101. The at least one tooth 111 is formed in the face side 109 of the illustrated cushion.

The at least one tooth 111 comprises a base 113, which is indicated by the dashed line in FIG. 6a, and the apex 114. The toothed profile achieves an improved seal by allowing for an increased amount of compression of the cushion for a given force, due to the reduced bearing surface area of the face side of the cushion compared to a cushion having no valleys 112. Furthermore, the apex 114 of the at least one tooth 111 may deflect relatively easily in any direction laterally across the face (i.e., vertically on the face, horizontally on the face, or any other direction across the face). In the cushion that is shown in FIG. 3, a particular point on the face side of the cushion cannot deflect sideways as easily due to support provided in the cushion material adjacent that point. Having contact points or areas 114 in contact with the outer sheath 102 provides improved flexibility of the cushion and an improved level of fit for a given sealing force.

Figure 7A:
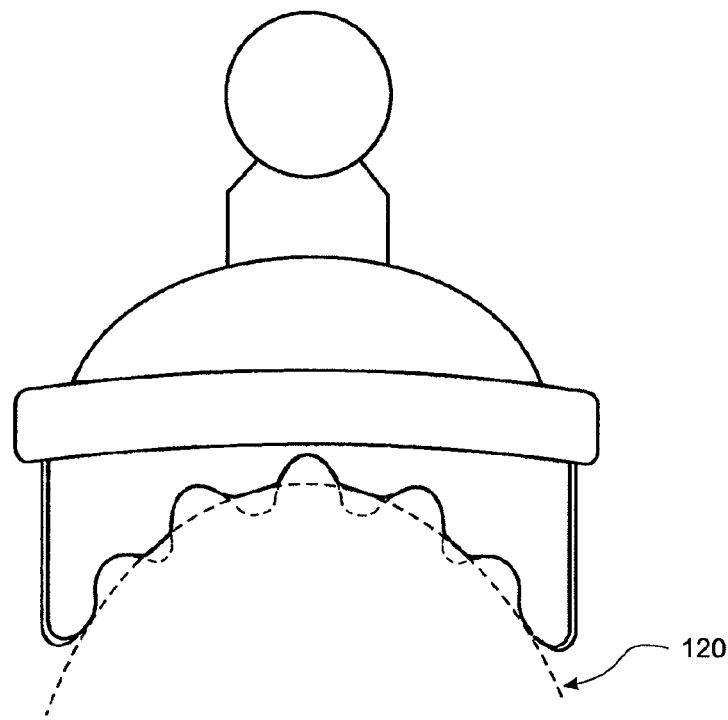
FIGS. 7a and 7b show bottom views of a face mask that is arranged and configured in accordance with certain features, aspects and advantages of one embodiment of the sealing interface of the present invention, wherein the chin and jaw line of two users indicated.
Figure 7B:
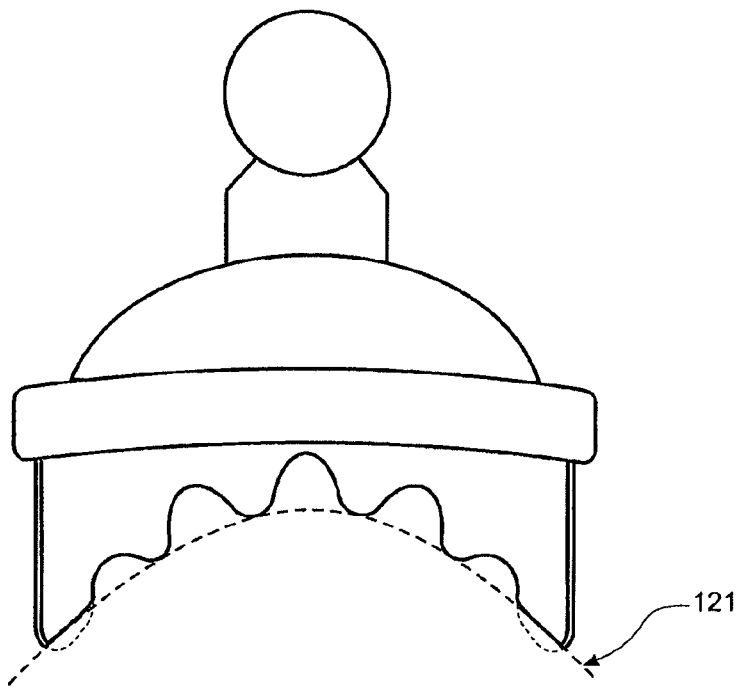

Due to the differing facial contours of different users, to achieve an effective seal on any given face, the seal should conform to a particular face easily. For example, when considering the shape of the chin region, one chin may be relatively broad and another chin may be relatively narrow. As shown in FIG. 7a, a first chin and jaw line is indicated by the dashed line 120. In order to conform to the line 120, each tooth 111 must be significantly compressed. Due to the reduced bearing area of the face side of the cushion comprising the toothed profile, the force required to press the seal 100 against the first chin and jaw line is lower than for a cushion without the toothed profile. FIG. 7b shows a second chin and jaw line 121, which is broader than the first chin and jaw line 120. In order to conform to a broader chin, the central portions of the toothed profile do not require as much compression. However, the apex 114 of the teeth 111 of the toothed profile 110 provides contact support against the outer sheath 102 at positions around the periphery of the mask seal 100. The toothed profile 110 provides more contact points than the prior art seal arrangement of FIG. 6f, and these contact points deflect and compress more easily than a prior art inner cushion without a toothed profile. Teeth that require a relatively high level of compression to conform to a user's face, as shown in FIG. 7a, will compress more easily compared to a cushion without a toothed profile. Teeth that require a relatively low level of compression or substantially no compression, as shown in FIG. 7b may still maintain contact with and provide support to the outer sheath. The toothed profile therefore provides an improved fit against a range of users with different facial contours.

The toothed profile achieves points of contact between the inner cushion 101 and the outer sheath 102 along the sealing interface perimeter. As the sealing interface is compressed against the face, the outer sheath 102 is stretched over the contact points and bridges the gaps between the contact points. The seal, at positions where the outer sheath 102 bridges valleys between teeth contact points, is relatively easy to deflect or compress a given amount of compression. The seal, where teeth contact the outer sheath 102, requires a higher level of force to compress for the same amount of compression.

Figure 11:
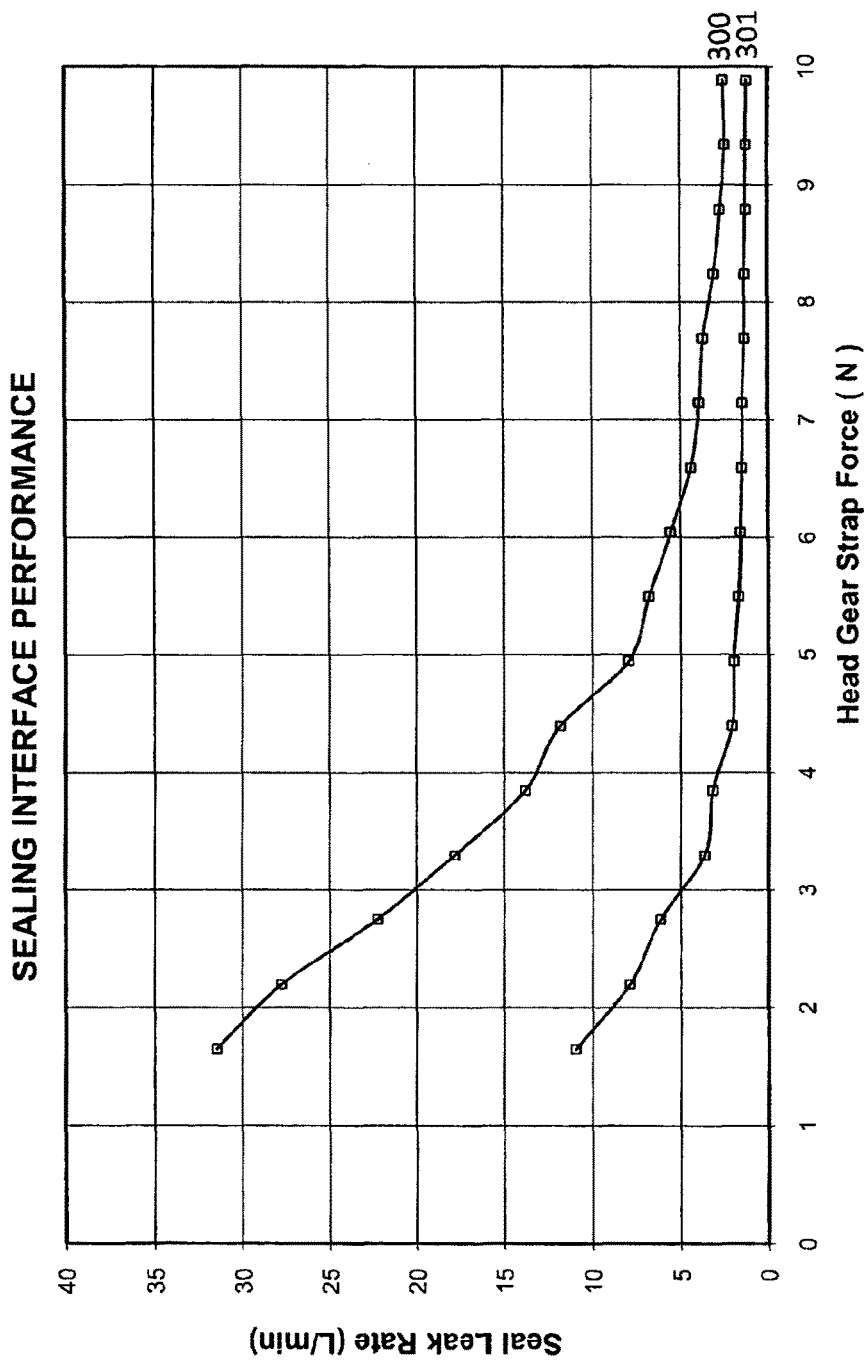
FIG. 11 is a chart showing data relating to leak rates comparing a prior mask sealing interface and a sealing interface incorporating a sealing interface cushion that is arranged and configured in accordance with certain features, aspects and advantages of the present invention.

The improvement in sealing efficiency of a seal interface incorporating the toothed inner cushion 101 is indicated in FIG. 11. FIG. 11 is a chart displaying the sealing efficiency of a sealing interface incorporating an inner cushion with a toothed profile compared to the sealing efficiencies of a sealing interface incorporating the same inner cushion but without a toothed profile. As shown in FIG. 11, a lower headgear strap force (i.e., a lower tension in the strap), which results in a lower mask seal force against the face of the user, is required to achieve a given leak rate. The upper trend line in FIG. 11, which is labelled 300, reflects data collected for a sealing interface comprising an inner cushion without a toothed profile. The lower trend line in FIG. 11, which is labelled 301, reflects data collected for a sealing interface comprising an inner cushion with a toothed profile in the face side of the inner cushion. For example, for a leak rate of about 10 liters per minute, the toothed cushion sealing interface requires a strap tension of less than about 2 Newtons while the same mask assembly incorporating the same inner cushion but without a toothed profile requires more than about 4 Newtons of strap force to reduce the leak rate to about 10 liters per minute. The data presented in FIG. 11 is averaged data collected from a range of different facial shapes.

Figure 12A:
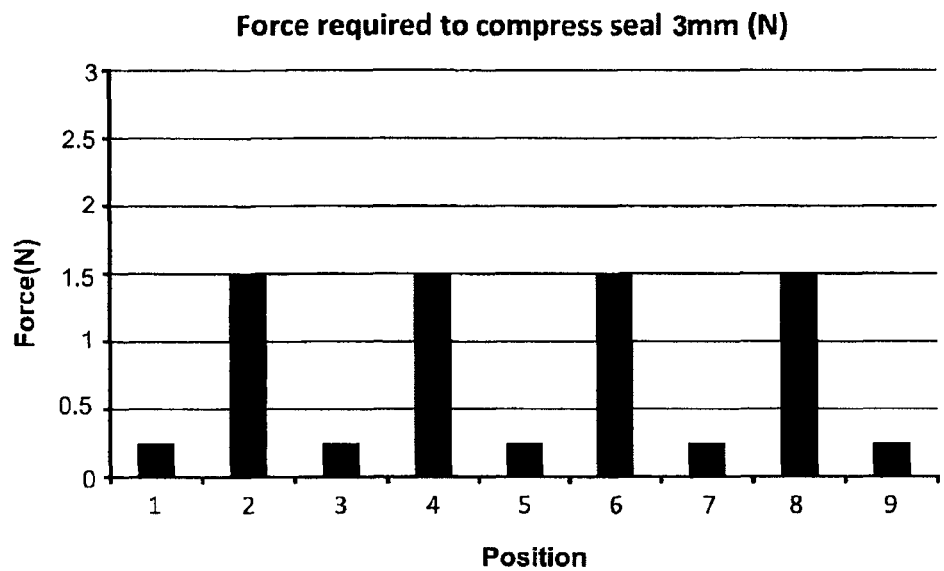
FIGS. 12a and 12b are charts showing a difference in compression force used to compress the sealing interface cushion that is arranged and configured in accordance with certain features, aspects and advantages of the present invention.
Figure 12B:
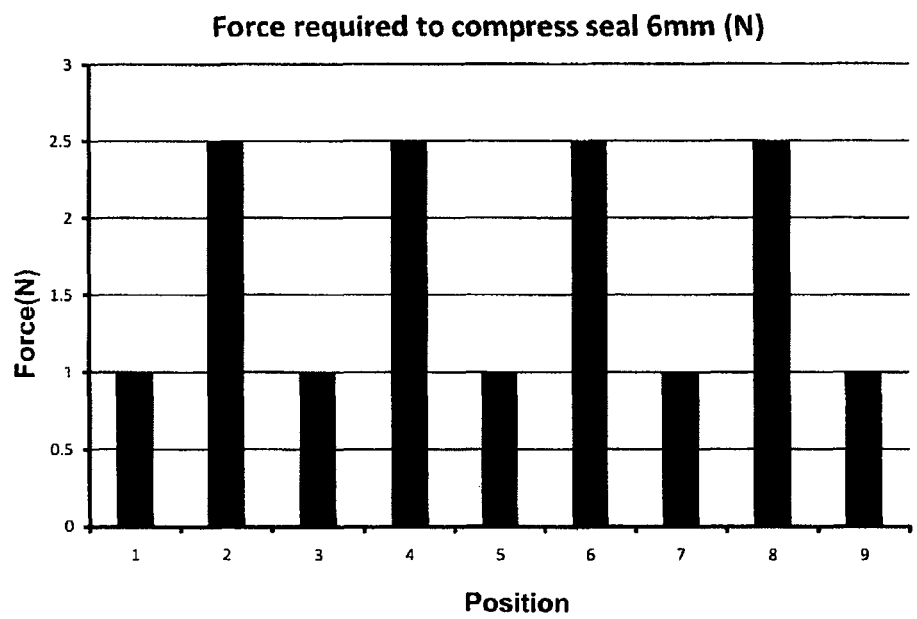

The effect of the toothed profile also can be seen in FIGS. 12a and 12b. A Newton meter fitted with a cone tip was used to measure the force required to compress the sheath and cushion of the seal 100 by a set distance. The cone tip used with the Newton meter had a base diameter of approximately 10 mm and a height of approximately 5 mm. Thus, the angle between the side of the cone tip and a plane perpendicular to the axis of the cone tip was about 45 degrees. The bars of each chart labelled with even numbers relate to positions along the mask seal at the apexes 114 of the toothed profile of the mask cushion 101. The bars labelled with odd numbers relate to positions along the mask seal 100 in between the apexes of the teeth of the toothed profile.

FIG. 12a shows a bar chart of the force required to compress different positions of the mask seal 100 by 3 mm. To compress the seal by 3 mm at the apex of a tooth requires a force of 1.5N. To compress the seal by 3 mm at positions where the sheath is initially unsupported by the cushion 101 (i.e., where the sheath is located over valleys 112 of the mask cushion 101), requires a force of around 0.25N. FIG. 12b shows the same bar chart as FIG. 12a but for a compression of the mask seal 100 by 6 mm.

The force required to compress a point on the seal 100 comprising the cushion without the teeth is similar to the force required to compress the seal at the apex 114 of the tooth for the seal with the cushion 101 having the toothed profile 110. For example, to compress a point on the seal, the seal having the sheath and the cushion without teeth, by 6 mm will require approximately 2.5N of force.

The charts of FIGS. 12a and 12b show how the overall force required to compress the seal 100 of the mask is reduced with the introduction of the toothed profile, while the toothed profile maintains support for the cushion at different points along the perimeter of the seal. Also, the charts of FIGS. 12a and 12b show how the differences between forces at different points change with increased compression. As the amount of compression of the seal 100 is increased, the ratio of the force to compress the seal at the tooth over the force to compress the seal at the cushion gap 112 reduces. For example, for the 3 mm compression shown in FIG. 12a, the ratio is 6 (i.e., the force required to compress the seal at the tooth is six times the force required to compress the seal at the tooth gap), with the outer sheath 102 in contact with the cushion 101 at the apexes 114 of the toothed profile. For the compression of 6 mm shown in FIG. 12b, the force required to compress the seal at the tooth is 2.5 times the force required to compress the seal at the tooth gap, with the outer sheath 102 in contact with the cushion 101 at the apexes of the toothed profile. As the amount of seal compression increases further, the ratio tends towards 1.

FIGS. 6a through 6e are bottom views of face masks incorporating various embodiments of the sealing interface 100 with the sealing interface in the uncompressed state. The sealing interface 100 is in the uncompressed state when not being used. FIGS. 6a to 6e show the sheath 102 and the cushion 101 generally spaced apart when in the uncompressed state. However, the apex 114 of any one or more teeth 111 may contact the outer sheath 102 when the interface seal 100 is in the uncompressed state, with the valley areas 112 not contacting the outer sheath 102.

The toothed profile 110 may comprise a single tooth, as shown in FIG. 6b. Alternative embodiments may include two, three, or more teeth, as shown in FIGS. 6c to 6e. The preferred embodiment has a toothed profile in the chin region consisting of at least about four teeth, as shown in FIG. 6a. Each tooth can be formed on the side 109 of the cushion that bears against the face of the user when in use.

Figure 8A:
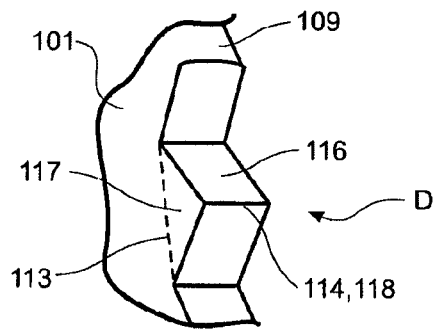
FIGS. 8a-8j show perspective views of various embodiments of a tooth profile for a toothed portion of a sealing interface cushion, which embodiments are arranged and configured in accordance with certain features, aspects and advantages of the present invention.
Figure 8B:
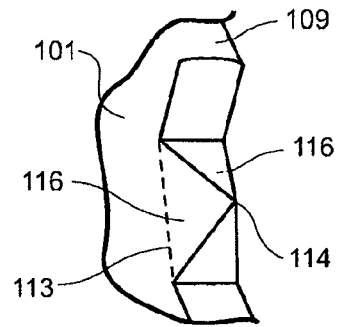
Figure 8C:
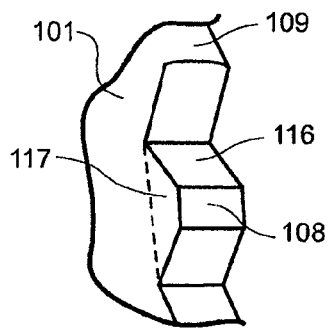
Figure 8D:
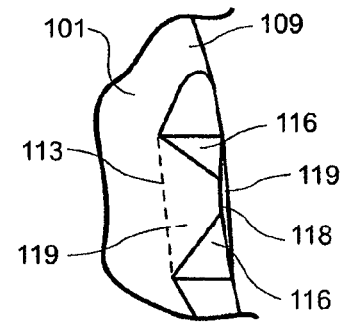
Figure 8E:
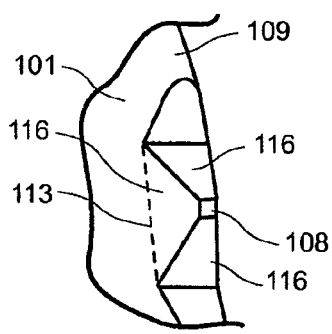
Figure 8F:
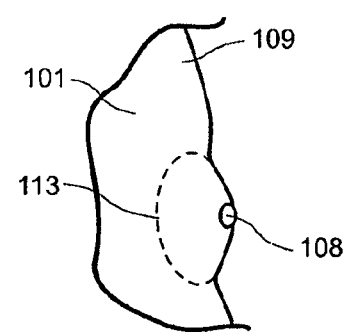
Figure 8G:
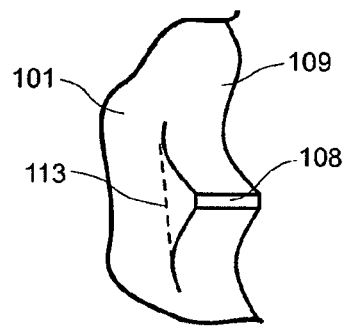
Figure 8H:
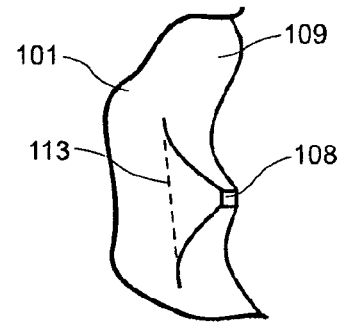
Figure 8I:
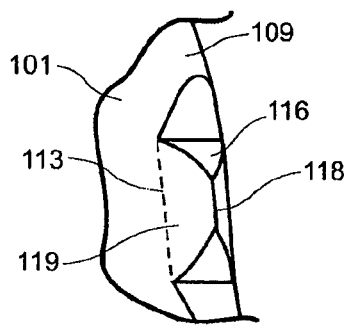
Figure 8J:
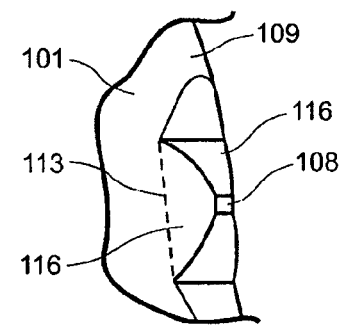

Various tooth profiles are shown in FIGS. 8a to 8j. The at least one tooth preferably comprises four sides 116 as shown in FIGS. 8b, 8d, 8e, 8h, 8i and 8j with the four sides 116 converging from the base 113 to the apex 114. The apex 114 may be formed by the four sides 116 converging to a point, as shown in FIG. 8b. Alternatively, the tooth may have two converging sides and two substantially parallel sides 117, as shown in FIGS. 8a, 8c and 8g, such that the apex is formed as a ridge 108, 118. The inner cushion of FIG. 5b comprises a toothed profile 110 with teeth 111 having a profile similar to the profile of FIG. 8a. Alternatively, the tooth may have four converging sides, with two opposing sides 119 converging at a lower angle of convergence compared to the other two opposing sides 116, such that the apex is formed as a ridge 118, as shown in FIGS. 8d and 8i. Alternatively, the base 113 of the tooth may be substantially rectangular, such that a ridge apex 118 is formed with four sides converging at the same angle.

Preferably, the apex 114, 118 is truncated to form an apex having an area 108 substantially reduced compared to the area of the base 113, as shown in FIGS. 8c, 8e, 8g, 8h and 8j. The inner cushion of FIG. 5a comprises a toothed profile 110 with teeth 111 in a lower portion of the cheek regions 55 of the inner cushion 101 having a profile similar to the profile of FIG. 8j. Alternatively, the tooth may be substantially frustoconical in shape, as indicated in FIG. 8f. Apex area 108 of the tooth of FIG. 8f may be rounded, similar to the tooth profile of FIG. 8j, for example.

The tooth profiles shown in FIGS. 8a to 8j may be symmetrical about a first plane and a second plane, the first plane being in line with the ridge 118 of FIG. 8a and the second plane being in line with the ridge 118 of FIG. 8d. Alternatively, the tooth 111 may have an asymmetrical shape, being symmetrical about one plane only, with the apex 114, 119 offset to one side of the tooth 111. The inner cushion 101 of FIG. 5a comprises a toothed profile 110 with teeth 111 in a chin region 56 of the inner cushion 101, wherein the teeth have a shape with the apex 114 being offset towards an outside surface of the inner cushion 101 (i.e., the outside surface at the bottom of the cushion, which is obstructed from view in FIG. 5a). Alternatively, the toothed profile 110 may comprise teeth having a shape with the apex 114,119 offset to two sides of the tooth 111, such that the tooth is asymmetrical with respect to the first and second planes described above.

As shown in FIGS. 8a through 8f, the sides 116, 117, 119 may be planar. Alternatively, as shown in FIGS. 8g through 8j, the sides 116, 119 may be convex or concave.

Any one or more combinations of the tooth shapes identified in FIG. 8a through FIG. 8j may be incorporated into the toothed profile of the inner cushion. Alternatively, the toothed profile 111 may include teeth with other shapes.

Figure 9:
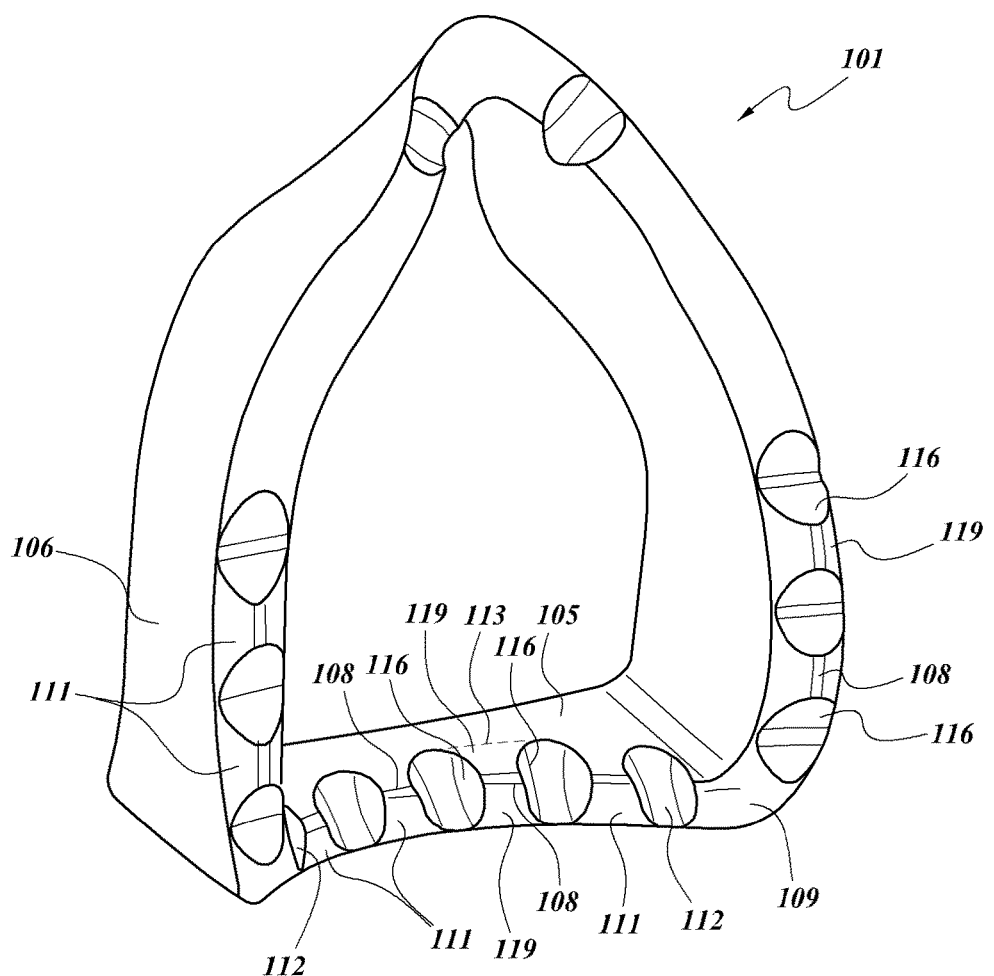
FIG. 9 is a perspective view of an embodiment of a sealing interface cushion that is arranged and configured in accordance with certain features, aspects and advantages of the present invention.

A preferred embodiment of the inner cushion 101 is shown in FIG. 9. The preferred toothed profile 111 of FIG. 9 comprises teeth 111 similar in shape to the teeth of FIG. 8h. However, the tooth profiles of FIGS. 8a through 8i are generally aligned centrally on the edge 109 of the inner cushion 101, as in the embodiments of FIGS. 5a and 5b. In the preferred embodiment of FIG. 9, the toothed profile 110 in the chin region 56 (refer to FIG. 4a) of the cushion 101 is formed by valleys 112 formed through the face side area 109 and inside surface 105 of the perimeter wall of the inner cushion 101. The valley portions 112 do not extend significantly through the outside surface 106 of the perimeter wall of the inner cushion. The teeth 111 in the chin region therefore generally are aligned inwards towards a centre of the inner cushion; one side 119 of the tooth 111 generally is coterminous with the inner surface 105 of the inner cushion, the other side 119 of the tooth generally is coterminous with the surface of edge 109. The apex area 108 of the tooth 111 is formed where the inner surface 105 meets the surface of edge 109. Sides 116 of the tooth 111 generally are coterminous with sides of the valley portions 112 on either side of the tooth 111.

The teeth 111 formed in the lower section of the cheek regions 55 of the cushion in FIG. 9 are formed in a similar way to the teeth in the chin region 56. Valley portions 112 are formed in the edge 109 without valley portions 112 significantly extending through the outer surface 106 of the cushion 101. Due to a curved shape of edge 109 in the lower cheek region, the apex 108 is located more outwardly compared to the apex 108 of the teeth 111 in the chin region 56, and sides 119 of the teeth in the lower cheek regions generally are coterminous with the curved surface of the edge 109 of the cushion, as shown in FIG. 9.

In the alternative embodiment of FIG. 10, the toothed profile consists of a comb type profile, where the bearing surface area of the edge 109 of the cushion is reduced by forming a series of teeth, steps or fingers, 125 in the edge 109. In one embodiment, the width of each tooth 126 is approximately equal to the width of each gap 127 between each tooth 126. In this embodiment, the bearing surface area of the cushion edge 109 is halved to reduce the compression force required to conform the cushion to the facial profile of a user. Alternatively, each gap 127 may be wider than each tooth 126 to decrease the bearing surface area even further. In an alternative embodiment, the width of each tooth may be wider than the width of each gap 127. In a further alternative embodiment, the tooth width and the gap width may vary for different sections of the edge 109 of the cushion, to result in portions of the cushion that are more easily compressed compared to other portions.

For example, the gaps 127 in the nasal bridge region may be more frequent than in other regions of the sealing interface to reduce the sealing force on the bridge of the nose of the user. The gaps 127 may be larger in the nasal bridge region than in other regions of the sealing interface to reduce the sealing force on the bridge of the nose of the user.

The width of the gaps 127 or the widths of the teeth 126 may vary around the perimeter of the sealing interface. The width of the tooth or the finger 125 may be chosen to be thin enough to allow buckling of the tooth under normal compression forces achieved during use. As the teeth 125 buckle under normal loads, the teeth provide a reduced level of support to the outer sheath, which allows improved conformance.

Preferably, the sealing interface comprises an inner cushion with any one of the toothed profiles described above in the chin region of the cushion. Preferably, the toothed profile consists of four teeth 111 or five valley portions 112 in the chin region, as shown in FIG. 9. Preferably, the sealing interface has an inner cushion with any one of the toothed profiles described above extending into a lower section of each cheek portion of the cushion. Preferably, the toothed profile consists of two teeth in the lower portion of each cheek region, as shown in FIG. 9.

Alternatively, the toothed profile may extend around the full perimeter of the cushion. In a further alternative embodiment, the cushion may incorporate the toothed profile in the nasal bridge region.

Preferably, the toothed profile has multiple teeth with a distance between the apexes of adjacent teeth of approximately 5 mm to 25 mm. Preferably, the distance between the apexes of adjacent teeth is less than about 20 mm. Most preferably, the distance between adjacent tooth apexes is less than about 15 mm. The depth of a tooth 111 (i.e., the distance between the apex 114 and the base 113) is approximately 3 mm to 10 mm. Preferably, the tooth depth is about 5 mm to 10 mm. The width of the base 113 of a tooth 111 can be approximately 2 mm to 25 mm. Preferably, the width of the base 113 of a tooth 111 is approximately 2 mm to 20 mm. Most preferably, the width of the base 113 of a tooth 111 is less than 15 mm.

Figure 8K:
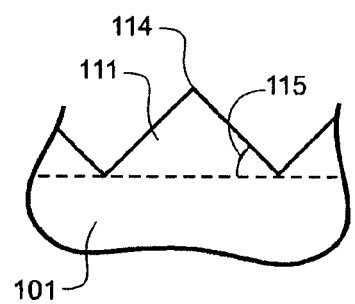
FIG. 8k is a side view of the tooth shape of FIG. 8a, when viewed in the direction of arrow D.

The angle of convergence 115 as shown in FIG. 8*k* can be high enough to provide a significant reduction in bearing surface area of the side 109 of the cushion that faces the face of the user in use. For example, an angle of convergence 115 of zero means that no teeth are formed in the side 109 of the cushion 101. Preferably, the angle of convergence is greater than about 35 degrees. Most preferably, the angle of convergence is greater than about 45 degrees.

The distance between the apexes of adjacent teeth may be described as the tooth pitch of the toothed profile. In the preferred embodiment, the ratio of the tooth depth over the tooth pitch is at least approximately 0.3. That is, the pitch is less than approximately three times the depth. Most preferably, the ratio of the depth and pitch is at least about 0.5 (i.e., the pitch is less than approximately twice the depth).

The cushion 101 preferably has a toothed profile 110 with a decreasing tooth depth as the toothed profile 110 extends from a central position of the toothed profile portion to an edge of the toothed profile portion, such as the construction shown in FIG. 6*a*.

The dimensions of the teeth of the toothed profile described above help achieve an improved seal. To seal in and around finer features and detailed contours of the face of the user, the relatively small pitch and high depth of the teeth perform well in sealing into creases and lines in the face of the user, such as smile lines and creases around the mouth and between the nose and cheek area of the user.

Certain features, aspects and advantages of the present invention may be implemented in a mask assembly having an integral cushion and outer sheath. However, the embodiments having an integrally formed cushion and outer sheath may not be preferred because the amount of movement between the outer sheath and the inner cushion is limited compared to when a separate cushion and outer sheath are used. Having a separate sheath and cushion provides relative movement between the sheath and the cushion resulting in an improved fit compared to if the sheath and cushion are secured together in an integrated construction.

Plurality of Spaced Apart Inner Cushions

Figure 15A:
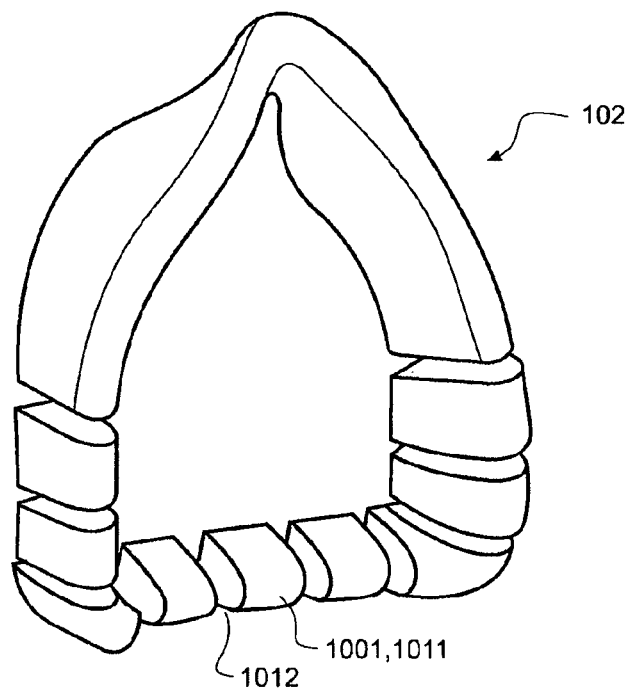
FIGS. 15a, 15b, 15d and 15e are perspective views of embodiments that are arranged and configured in accordance with certain features, aspects and advantages of the present invention, wherein the sealing interface cushion comprises a plurality of spaced apart cushions.
Figure 15B:
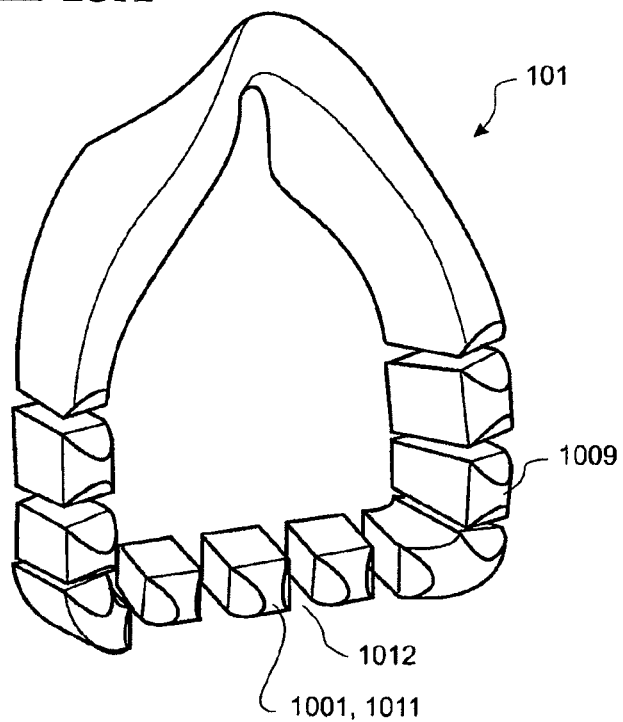

In an alternative embodiment shown in FIGS. 15*a* and 15*b*, the mask cushion 101 may be a plurality of cushions 1001 spaced apart to achieve a toothed profile generally comprising teeth 1011 and gaps 1012 between the teeth 1011.

Each cushion 1001 has a side 1009 that bears against the face of the user in use. As shown in FIG. 15*b*, side 1009 of at least one cushion 1011 may be shaped as previously described in relation to FIGS. 8*a* to 8*j* or may have any other suitable toothed profile, including any described herein.

The cushion 101 may comprise a plurality of cushions 1001 in the chin or upper lip region, the cheek regions, nasal bridge region, or completely around the perimeter of the mask seal 100.

Figure 10A:
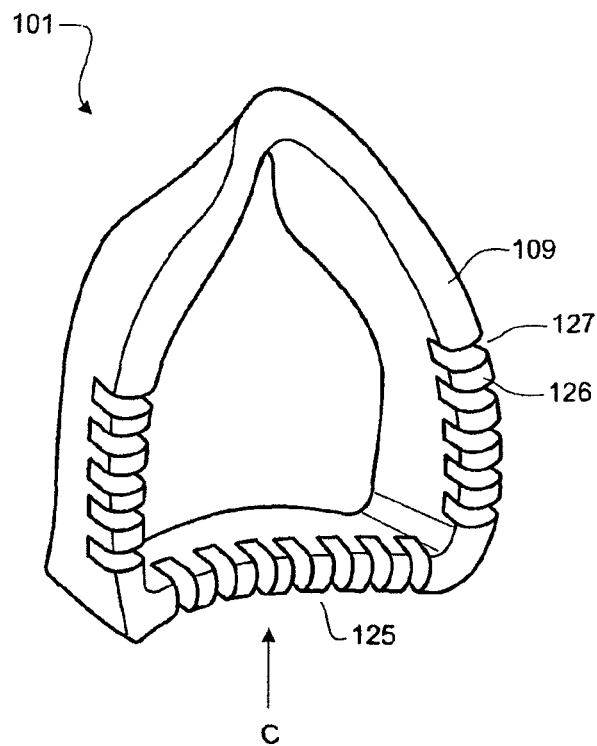
FIG. 10a is a perspective view of an embodiment of a sealing interface cushion that is arranged and configured in accordance with certain features, aspects and advantages of the present invention.
Figure 10B:
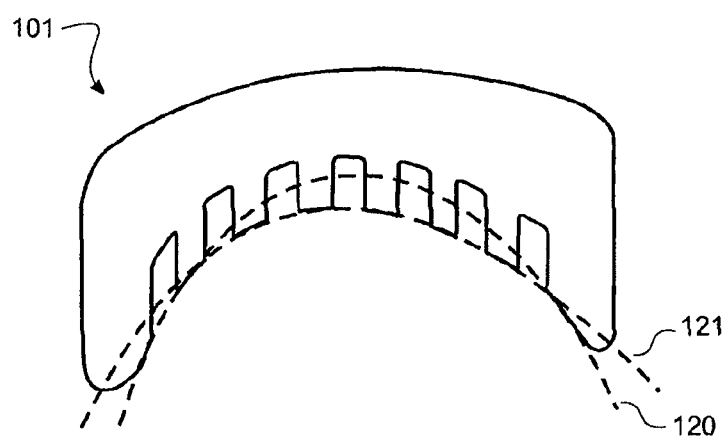
FIG. 10b is a bottom view of the sealing interface cushion of FIG. 10a viewed in the direction of arrow C.

The embodiment of FIG. 15*a* is similar in concept and operation to the embodiment shown in FIGS. 10*a* and 10*b*. For example, the removed portions 127 of the cushion of FIG. 10*a* may be removed to a sufficient depth such that, under normal operation, the mask seal 100 is not compressed further than the depth of the removed portions 127.

Figure 15C:
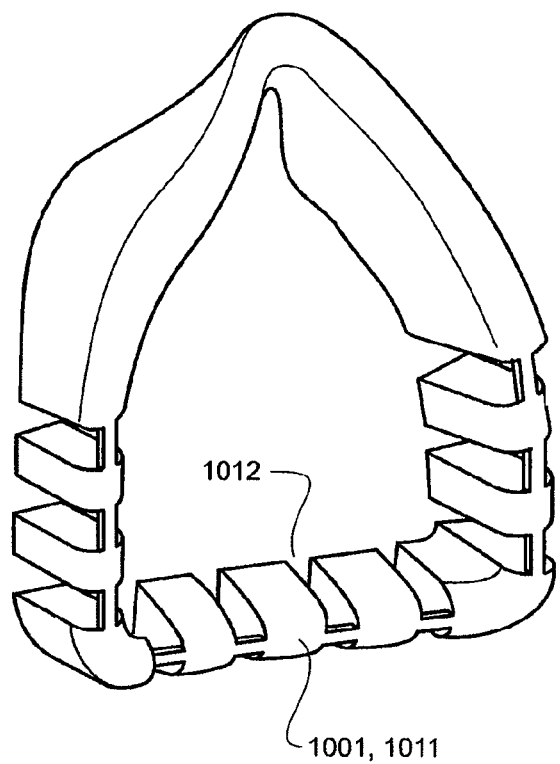
FIG. 15c is a perspective view of an embodiment that is arranged and configured in accordance with certain features, aspects and advantages of the present invention, wherein the sealing interface cushion comprises spaced apart cushions joined together by joining elements.

In the alternative embodiment of FIG. 15*c*, the plurality of cushions 1001 may be attached to one another to form a single cushion comprising cushion elements 1001 joined together by joining elements 1013. The cushion elements 1001 are sized to extend between the mask hollow body 22 and an inner surface of the side of the outer sheath that bears against the face of the user in use. The joining elements are sized to not extend between the hollow body 22 and the side of the outer sheath that bears against a user's face in use. The joining elements 1013 may be located to contact the outer sheath. For example, the joining elements 1013 may contact an inner surface of the side of the outer sheath that seals against the face of the user in use. In this case, the joining elements 1013 are sufficiently thin to result in a low force for a given amount of seal compression at a joining element 1013 compared to the force required to compress the seal by the same amount of compression at a cushion element 1001. Alternatively, the joining elements 1013 may be located to not contact the outer sheath.

Figure 15D:
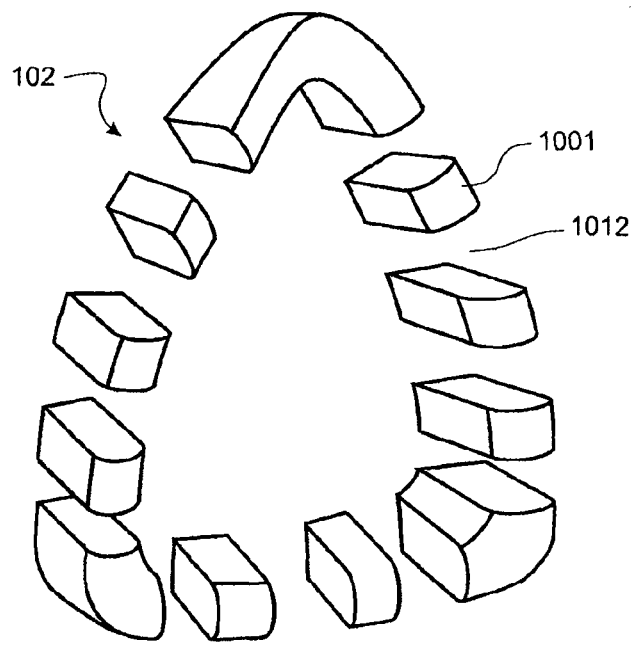
Figure 15E:
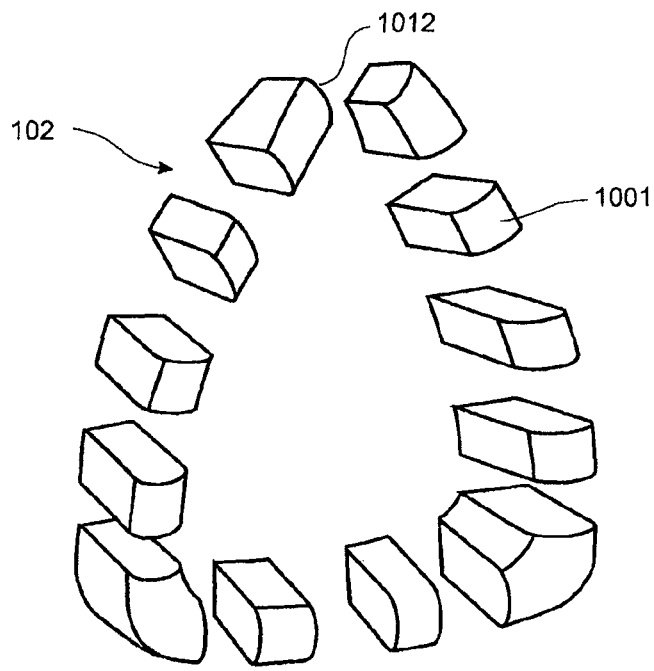

Further embodiments are illustrated in FIGS. 15*d* and 15*e*. In the embodiment of 15*d*, the inner cushion 102 comprises a plurality of cushions 1001 spaced apart around the full perimeter of the sealing interface with gaps 1012 between adjacent cushions 1001. In the embodiment of FIG. 15*e*, the individual cushions 1001 are arranged such that a gap 1012 is located in the nasal bridge region of the sealing interface.

The perimeter length of the gaps 1012 between the plurality of cushions 1001 may be varied to result in portions of the cushion that are more easily compressed compared to other portions.

Hole Profile

Figure 13A:
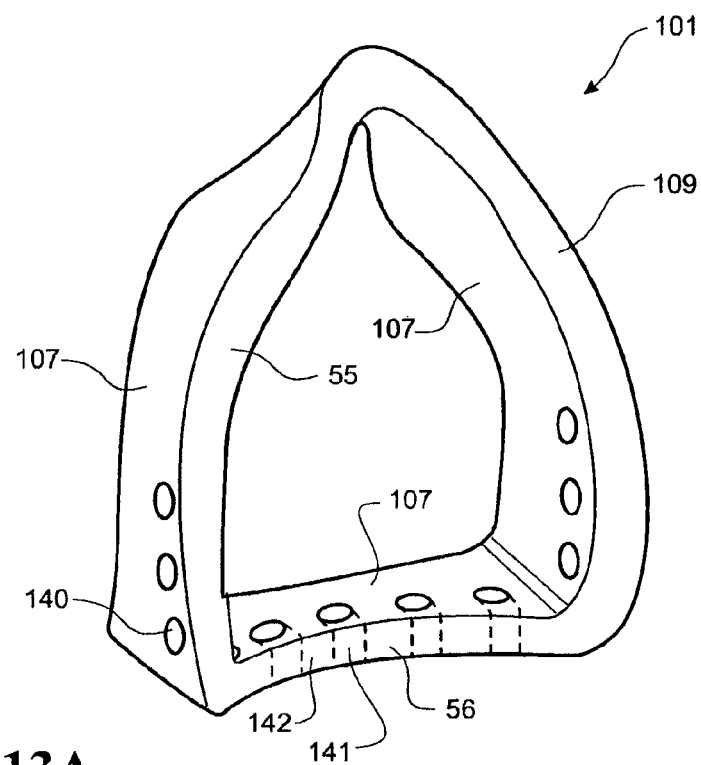
FIGS. 13a and 13b are perspective views of embodiments of a sealing interface cushion that is arranged and configured in accordance with certain features, aspects and advantages of the present invention and that incorporates a hole profile with holes through a wall of an inner cushion.
Figure 13B:
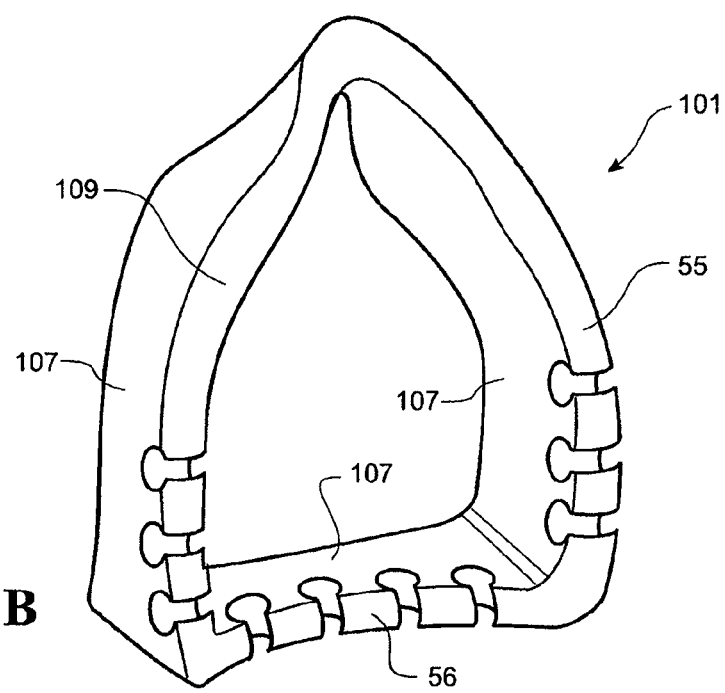

In a further alternative embodiment, as shown in FIG. 13*b*, a toothed profile in the face side of the inner cushion can be achieved by holes 140 that extend through the wall 107 of the inner cushion. The holes break the surface of the face side 109 of the inner cushion.

In the alternative embodiment of FIG. 13*a*, the holes 140 through the wall 107 of the inner cushion do not break the surface of the face side of the cushion. The holes 140 are provided near the side 109 that bears against the face of the user. The portions 141 adjacent to the holes 140 compress more easily compared to the portions 142 located between the adjacent holes 140. The holes 140 may be circular or have any other suitable shape, such as oval as shown in FIG. 13*a*, for example.

Figure 14A:
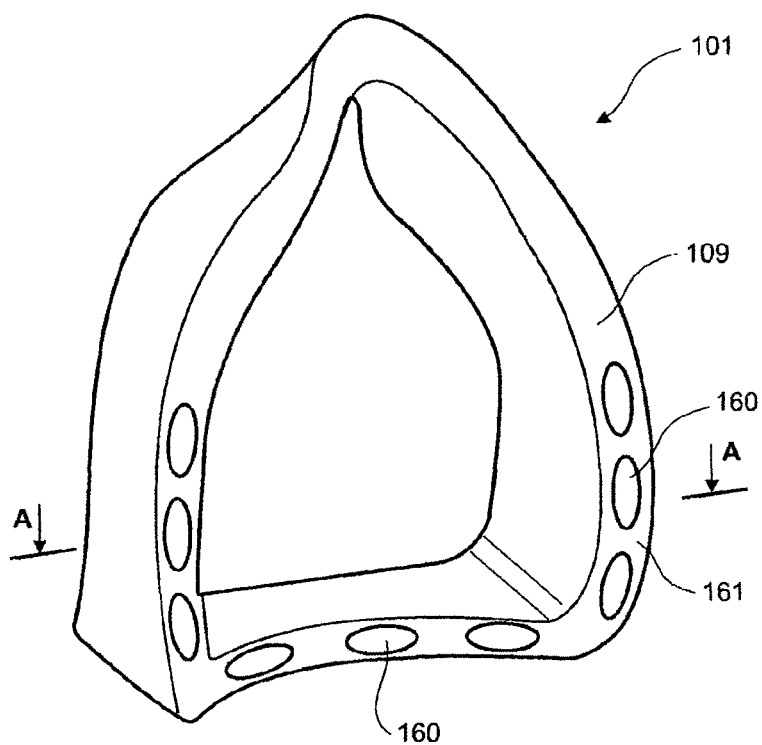
FIGS. 14a, 14c and 14d are perspective views of embodiments of a sealing interface cushion that are arranged and configured in accordance with certain features, aspects and advantages of the present invention and that incorporates holes or cavities in a side of the sealing interface cushion that faces a user's face in use.
Figure 14B:
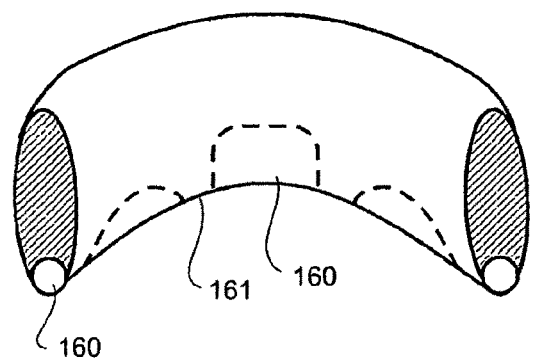
FIG. 14b is a cross sectional view of the sealing interface cushion of FIG. 14a, when viewed in the direction of arrows A.

In an alternative embodiment of FIGS. 14*a* and 14*b*, the holes or cavities 160 are provided in the side 109 of the cushion that bears against the face of the user in use. The cavities result in portions of the seal 100 that compress more easily compared to portions of the seal at positions of the cushion 161 in between the cavities 160.

Figure 14C:
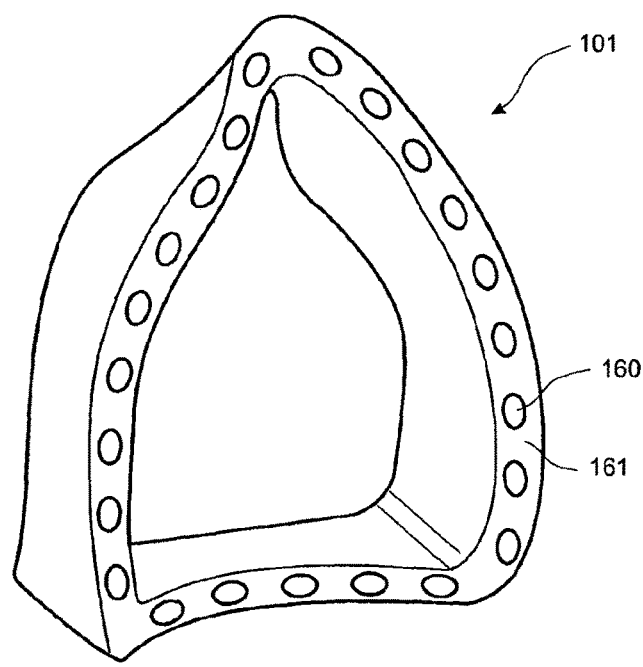
Figure 14D:
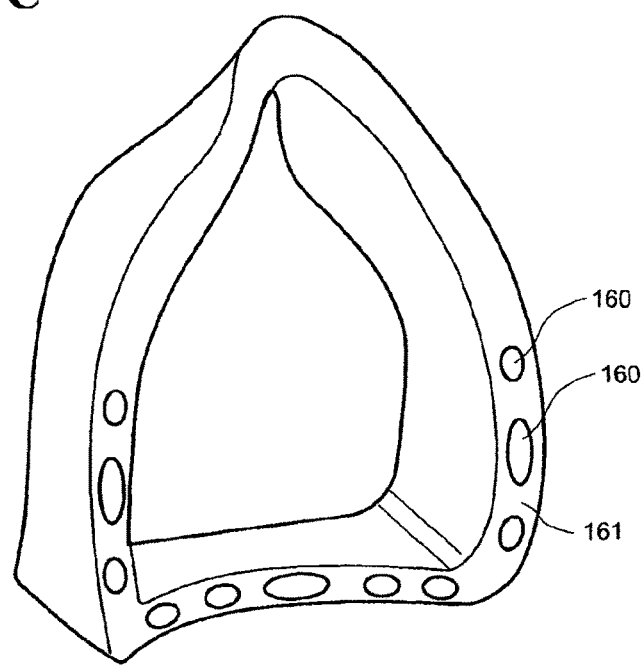

The cavities 160 may vary in perimeter length around the perimeter of the inner cushion to result in portions of the cushion perimeter that are more easily compressed compared to other portions, as shown in FIG. 14*d*. The cavities 160 may vary in depth around the perimeter of the inner cushion to result in portions of the cushion that are more easily compressed compared to other portions, as shown in FIG. 14*b*. The cavities 160 may vary in width across the side 109 of the cushion around the perimeter of the inner cushion to result in portions of the cushion that are more easily compressed compared to other portions, as indicated in FIG. 14*d*, for example.

The areas 161 between and around the cavities 160 may form a continuous contact surface in contact with the outer sheath. The cavities 160 may have an asymmetric shape as indicated in the cross sectional view of FIG. 14*b*.

The cavities 160 may be positioned around the full perimeter of the cushion, with each cavity being spaced apart by the areas 161 between the adjacent cavities, as shown in FIG. 14c. Alternatively, the cavities 160 may only be provided in particular regions of the cushion. For example, the cavities 160 may be provided in the upper lip region of the cushion.

The perimeter length of spacing 161 between the cavities 160 may be varied. Alternatively, spacing between the cavities 160 may have equal length around the perimeter of the inner cushion.

A sealing interface comprising an inner cushion with a toothed profile on the face side of the inner cushion supporting an outer sheath achieves an improved sealing interface having a reduced leak rate for a given interface headgear strap tension compared to prior sealing interfaces.

Certain features, aspects and advantages of the present invention have been described with reference to a number of embodiments. It is to be understood that these embodiments are merely illustrative. Modifications may be made thereto without departing from the scope of the invention.

What is claimed is:

1. A sealing interface for use as part of an apparatus for supplying a flow of respiratory gases to a user, the sealing interface comprising:
   an outer sheath and an inner cushion, the outer sheath being formed of thin resilient rubber and the inner cushion being formed of foam or gel, in use the outer sheath covering the inner cushion, the outer sheath having a sheath first side, the sheath first side substantially sealing against the user's face, the inner cushion comprising a sidewall and a face side, the face side comprising a face contacting surface configured to press the sheath first side against the user's face, and
   at least two cavities being defined within the face side of the inner cushion and recessed from the face contacting surface, the at least two cavities resulting in portions of the sealing interface that compress more easily compared to portions of the sealing interface at positions in between the at least two cavities.

2. The sealing interface as claimed in claim 1, wherein the at least two cavities in the inner cushion are disposed in the face side of the inner cushion spaced apart substantially around a full perimeter of the inner cushion.

3. The sealing interface as claimed in claim 1, wherein the sheath first side and the face side of the inner cushion have a nasal bridge region, one of an upper lip region and a chin region, and a left cheek region and a right cheek region extending between the one of the nasal bridge region and the upper lip or chin region, and
   the at least two cavities in the inner cushion are spaced apart around the perimeter of the inner cushion in the one of the upper lip region and the chin region.

4. The sealing interface as claimed in claim 3, wherein the at least two cavities in the inner cushion also are spaced apart around the perimeter of the inner cushion in a lower portion of each of the left and right cheek regions.

5. The sealing interface as claimed in claim 3, wherein the at least two cavities in the inner cushion are spaced apart around the perimeter of the inner cushion in the nasal bridge region.

6. The sealing interface as claimed in claim 1, wherein the at least two cavities in the inner cushion vary in perimeter length around the perimeter of the inner cushion to result in portions of the cushion perimeter that are more easily compressed compared to others portions.

7. The sealing interface as claimed in claim 1, wherein the at least two cavities in the inner cushion vary in depth around the perimeter of the inner cushion to result in portions of the cushion that are more easily compressed compared to others portions.

8. The sealing interface as claimed in claim 1, wherein the at least two cavities in the inner cushion vary in width across the face side of the cushion around the perimeter of the inner cushion to result in portions of the cushion that are more easily compressed compared to others portions.

9. The sealing interface as claimed in claim 1, wherein areas between and around the cavities form a continuous contact surface in contact with the outer sheath.

10. The sealing interface as claimed in claim 1, wherein the at least two cavities in the inner cushion have an asymmetric shape.

11. The sealing interface as claimed in claim 1, wherein a perimeter length of spacing between cavities is varied.

12. A mask assembly for use as part of an apparatus for supplying a flow of respiratory gases to a user comprising:
    a mask body having an inlet through which the flow of respiratory gases are provided to an interior of the mask body, the inlet adapted to in use be connected to a gases conduit, and
    a sealing interface coupled to the mask body, the sealing interface comprising:
    a thin resilient rubber outer sheath and a foam or gel inner cushion as claimed in claim 1, in use the outer sheath covering the inner cushion, the outer sheath having a sheath first side, the sheath first side substantially sealing against a user's face, a face side of the inner cushion resiliently supporting at least a portion of the sheath first side.

* * * * *